(12) United States Patent
Espino

(10) Patent No.: US 12,108,895 B2
(45) Date of Patent: Oct. 8, 2024

(54) OPERATING ROOM FLOOR MAT WITH PROTECTIVE SHEET TO COVER SURGICAL EQUIPMENT FOOT PEDALS

(71) Applicant: Jose Gustavo Espino, Alexandria, VA (US)

(72) Inventor: Jose Gustavo Espino, Alexandria, VA (US)

( * ) Notice: Subject to any disclaimer, the term of this patent is extended or adjusted under 35 U.S.C. 154(b) by 268 days.

(21) Appl. No.: 17/363,978

(22) Filed: Jun. 30, 2021

(65) Prior Publication Data

US 2023/0000272 A1   Jan. 5, 2023

(51) Int. Cl.
| | |
|---|---|
| *A47G 27/02* | (2006.01) |
| *A47G 27/04* | (2006.01) |
| *A61B 17/00* | (2006.01) |
| *A61G 13/10* | (2006.01) |

(52) U.S. Cl.
CPC ..... *A47G 27/0206* (2013.01); *A47G 27/0412* (2013.01); *A61B 17/00* (2013.01); *A61G 13/102* (2013.01); *A61B 2017/00973* (2013.01)

(58) Field of Classification Search
CPC .. A47G 7/0206; A47G 7/0412; A47G 13/102; A61B 7/00; A61B 2017/00973
See application file for complete search history.

(56) References Cited

U.S. PATENT DOCUMENTS

| | | | | |
|---|---|---|---|---|
| 5,028,468 A | * | 7/1991 | Taylor | A61B 46/10 428/192 |
| 8,209,811 B2 | * | 7/2012 | Jordan | A61L 2/232 422/292 |
| 10,371,370 B2 | * | 8/2019 | Baldwin | A61B 90/30 |
| 10,527,277 B2 | * | 1/2020 | Baldwin | A61B 90/92 |
| 10,549,897 B2 | * | 2/2020 | Sacks | B65D 81/18 |
| 2005/0126577 A1 | * | 6/2005 | Griesbach, III | A61B 46/00 128/849 |
| 2013/0240402 A1 | * | 9/2013 | Campista | A61B 6/4423 428/34.1 |
| 2018/0214331 A1 | * | 8/2018 | Borden | A47G 27/0206 |
| 2020/0080718 A1 | * | 3/2020 | Baldwin | G05G 1/30 |

FOREIGN PATENT DOCUMENTS

JP   H0349596   *   3/1991

OTHER PUBLICATIONS

Translation used by examiner of H0349596 (Year: 1991).*

* cited by examiner

*Primary Examiner* — Monica E Millner
(74) *Attorney, Agent, or Firm* — BACON&THOMAS,PLLC

(57) ABSTRACT

An operating room floor mat includes a main body and a protective sheet that is secured around to the main body around a perimeter of the sheet. A section of the perimeter is left unsecured to form an opening of a pocket into which at least one foot pedal is inserted, and through which a cable connection between the foot pedal and surgical equipment extends. Placement of the foot pedal into the pocket protects the foot pedal from blood or irrigation fluid dripping from an operating table without interfering with operation of the foot pedal.

4 Claims, 2 Drawing Sheets

OPERATING ROOM FLOOR MAT WITH PROTECTIVE SHEET TO COVER SURGICAL EQUIPMENT FOOT PEDALS

BACKGROUND OF THE INVENTION

1. Field of the Invention

The invention relates to an operating room floor mat for placement on the floor adjacent an operating room table, and in particular to a floor mat having a pocket to protect foot pedals from fluids such as irrigation fluid or blood that drip, splatter, or spill from the table during an operation. The foot pedals are used to control equipment such as suction units, shavers, cutting tools, drills, lasers, and other devices or instruments used for arthroscopic and other surgical procedures.

2. Description of Related Art

Foot pedals connected to surgical equipment are conventionally placed on the floor adjacent an operating table, so that a physician or assistant can control the equipment while performing a surgical procedure on the patient.

A problem with placement of the pedals close to the operating table, where the pedals can be reached by the operator, is that the placement exposes the pedals to fluids such as blood and irrigation fluid that run off the patient and the operating table. Where the amount of fluid is high enough to affect operation of the pedals, it is conventional practice for operating room personnel to cover the pedals with plastic bags. However, the plastic bags used to protect the pedals are subject to slippage or rupture as the operator moves his or her feet during the operation, leaving the pedals exposed to waste fluid that can damage the pedals as well as interfere with their operation. In addition, the bags add to the medical waste generated during the procedure, as well as to the time required to prepare for the procedure, and to clean up after the procedure.

While it is well-known to provide floor coverings to facilitate cleaning and absorb excess fluids so that the clinician does not slip on the fluids, such mats do not conventionally protect the pedals, which are placed on the mats in an exposed position. As a result, the pedals continue to be exposed to waste fluids from the operating table unless covered by plastic bags. FIG. 3 shows an example of conventional floor coverings 10 and the fluids 11 that accumulate on the floor mats during an operation.

SUMMARY OF THE INVENTION

It is accordingly a first objective of the invention to overcome the above-described disadvantages of conventional operating room equipment and procedures relating to surgical equipment foot pedals, by providing a way to protect the foot pedals that is convenient, safe, and sanitary, and that does not interfere with operation of the pedals.

It is a second objective of the invention to provide protection for surgical equipment foot pedals that is inexpensive and reusable.

These objections are achieved, in accordance with the principles of an exemplary embodiment of the invention, by modifying an operating room floor mat to add a protective sheet that is secured to the main body by fixing a perimeter of the sheet to the main body, with a section of the perimeter being left unsecured to form a pocket with an opening into which at least one foot pedal is inserted before beginning the surgical procedure such that the cable connection between the foot pedal and surgical equipment extends through the opening, and such that the protective sheets protects the foot pedal from blood or irrigation fluid dripping from the operating table without interfering with operation of the pedal.

Preferably, the protective sheet is transparent in at least the area(s) where the at least one foot pedal is placed, and is made of a durable, relatively high friction plastic material that can withstand pressure or forces exerted by the operator during operation of the pedal, and that allows fluids to be easily wiped off of or otherwise removed from the surface of the protective sheet as necessary during the surgical procedure.

DETAILED DESCRIPTION OF THE PREFERRED EMBODIMENTS

Figure 1:
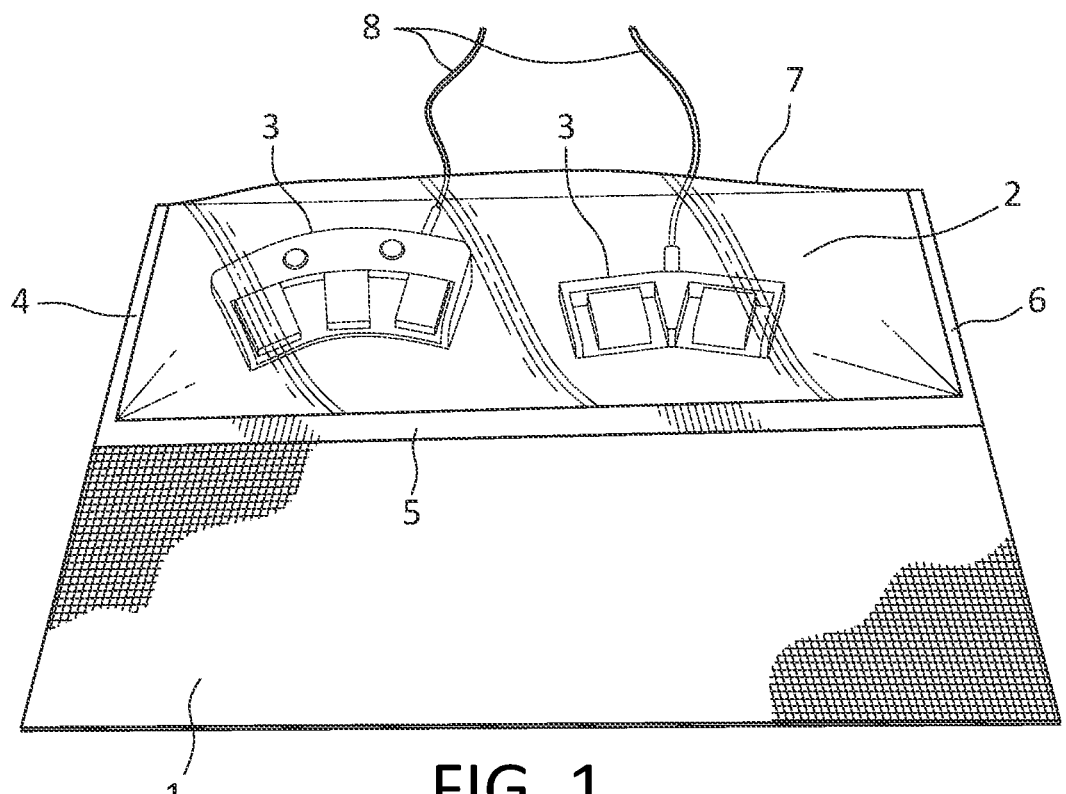
FIG. 1 is a perspective view of an operating room floor mat that has been modified to include protection for foot pedals in accordance with the principles of a preferred embodiment of the invention.
Figure 3:
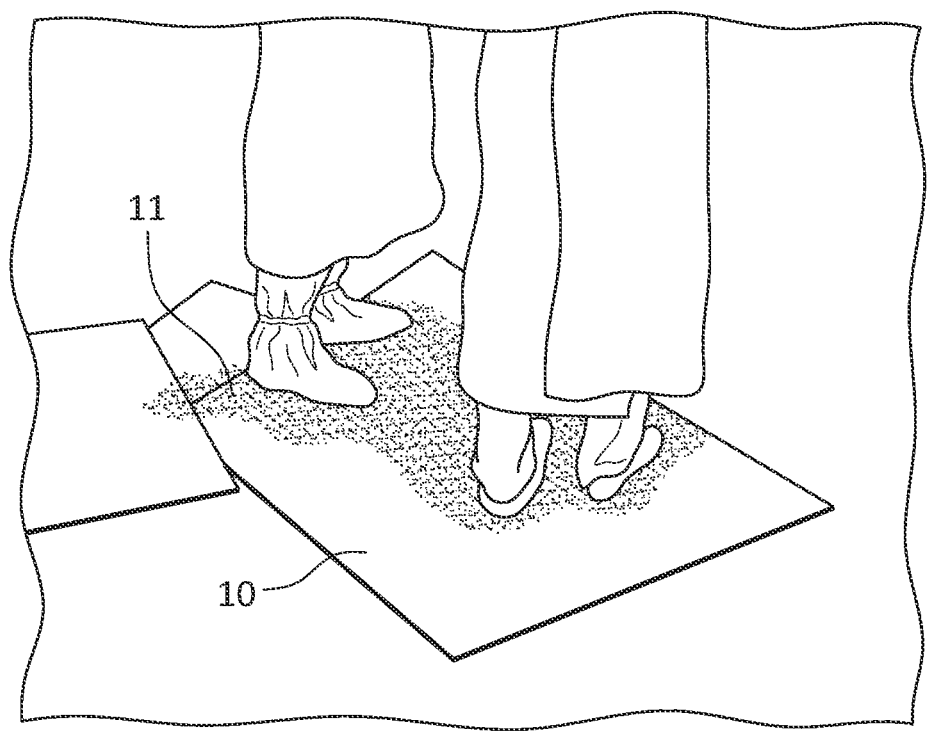
FIG. 3 is a photograph showing conventional operating room floor mats that are exposed to fluids during a surgical procedure.

As shown in FIG. 1, an operating room floor mat constructed in accordance with the principles of the present invention includes a main body 1 and a pedal protection sheet or layer 2.

Main body 1 is conventional, and may be made of a fabric or sheet material that preferably absorbs fluids such as blood and saline, is easy to clean, and is slip resistant both to prevent the mat from sliding with respect to the floor and to prevent persons standing on the mat and wearing surgical booties from slipping or tripping as they move around during a surgical procedure.

The main body 1 may optionally include a layer of high friction material such as rubber or an adhesive backing (not shown) to prevent sliding of the main body with respect to the floor, as well as foam or gel layers to absorb fluids and relieve fatigue or discomfort while standing on the mat for extended periods of time. In addition, the main body 1 of the mat may optionally have anti-microbial or anti-bacterial properties, and be washable so that it can be reused. It will be appreciated that numerous floor mat constructions and materials are currently available, and that the invention is not to be limited to a particular main body construction or material.

Unlike the main body 1, the pedal protection sheet or layer 2 is not conventional. It is preferably made of a transparent plastic sheet material such as acetate or low density polyethylene. The transparency of the sheet material permits the user to visually locate a pedal positioned below the material in order to operate the pedal, although it is also within the scope of the invention to make the plastic sheet of an opaque material having transparent sections in areas where a foot pedal or foot pedal unit is to be placed. The material of the pedal protection sheet or layer 2 should be durable enough to withstand pressure caused by stepping on the pedal in order to operate equipment controlled by the pedal, and should allow fluids to be wiped off of the sheet while also resisting slippage when wet.

According to the principles of the preferred embodiment of the invention, the pedal protection sheet or layer 2 is secured the main body 1 along its perimeter, leaving an unsecured section that forms the opening of a pocket into which at least one foot pedal or pedal unit is placed. As illustrated in FIG. 1, the protective sheet or layer 2 is secured to the main body 1 along three sides 4-6. The fourth side 7 of the protective sheet or layer is unsecured to form the opening of the pocket, and to permit insertion of pedal devices 3 and passage of pedal-connecting cables 8.

The pedal protection sheet or layer 2 may be secured on the three sides 4-7 by stitching, adhesives, single or double sided tape, a removable fastener such as Velcro™, or any other suitable fastener or fastening means. It will be appreciated that the invention is not to be limited to a particular means for fastening the protection sheet or layer 2 to the main body 1, although it is preferable that the fastener be resistant to infiltration or passage of fluids into the pocket, and sufficiently strong to hold the pedal protection sheet or layer 2 in place on the main body 1 while being stepped on and subjected to stresses resulting from operation of the pedals or movement of an operator or clinician during a procedure.

Those skilled in the art will appreciate that the illustrated pedal devices 3 are illustrative only, and that the pocket formed by the protective sheet or layer 2 may be arranged to accommodate any pedal devices that might be used in an operating room, as well as different numbers of pedal devices. For example, although two pedal devices 3 are shown in FIG. 1, the pocket may also accommodate just one pedal device, or more than two pedal devices, depending on the number and nature of surgical equipment to be controlled.

Figure 2A:
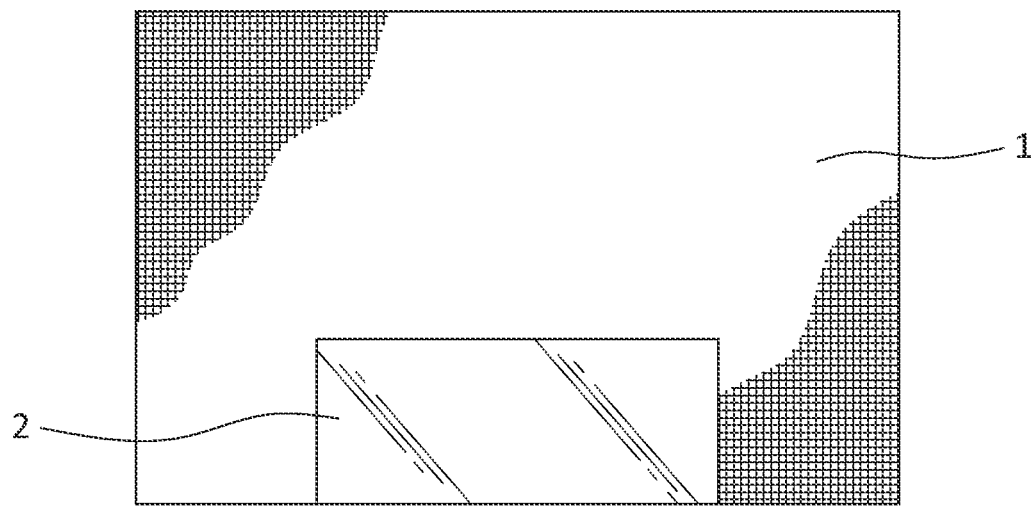
FIGS. 2A and 2B show alternative shapes for the operating room floor mat of FIG. 1.
Figure 2B:
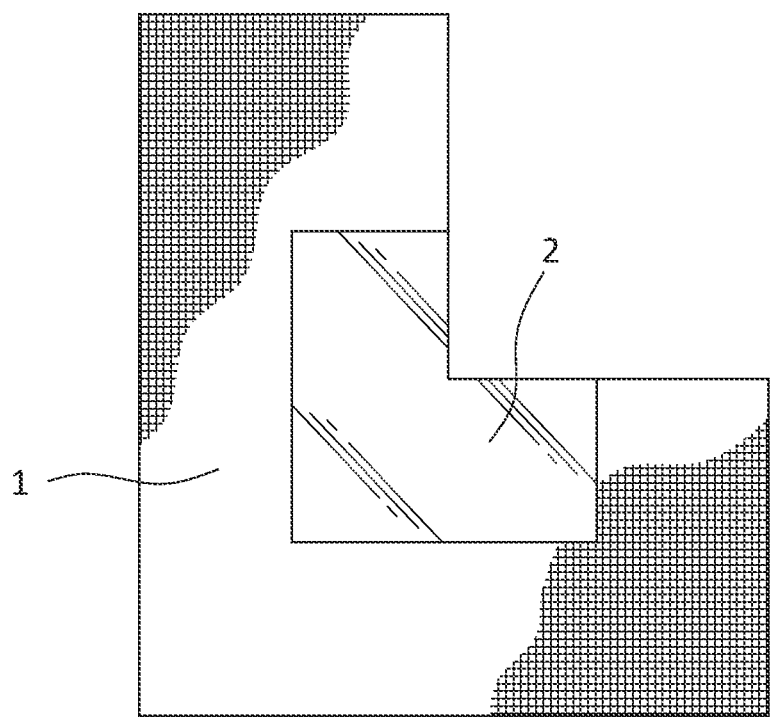

Although the main body 1 and protective sheet or layer 2 are illustrated in FIG. 1 as square, with the protective sheet or layer 2 covering approximately half the area of the main body 1, it will be appreciated that the main body 1 and the protective sheet 2 may have other shapes. For example, the protective sheet or layer 2 may cover a smaller area of the main body 1, as shown in FIG. 2A, and/or the main body 1 and/or the protective sheet or layer 2 may have an L-shape, as shown in FIG. 2B. As a result, the shapes and sizes of the main body 1 and the protective sheet or layer 2 may be freely varied without departing from the scope of the invention.

Although a specific embodiment of the invention has been described with sufficiently particularity to enable those skilled in the art to make and use the invention, it will be appreciated that the invention is not to be limited to the exemplary embodiment, but is intended to encompass any variations and modifications of the concepts described above that might occur to those skilled in the art. For example, the materials, shapes, sizes, and construction of the main body 1 and protective sheet or layer 2 may be varied as described above, including use of removable fasteners to attach the protective sheet or layer 2 to the main body 1 in order to facilitate cleaning. In addition, it is possible that the foot pedal might utilize a wireless or Bluetooth connection rather than a cable, in which case the foot pedal can still advantageously be placed in the pocket formed by the protective sheet or layer 2. Consequently, it is intended that the scope of the invention should be limited solely by the scope of the appended claims.

What is claimed is:

1. An operating room floor mat with a pocket arranged to receive and protect at least one foot pedal for controlling surgical equipment during a surgical procedure on a patient situated on an operating room table, comprising:
   a main body arranged to be placed on a floor of an operating room adjacent the operating room table; and
   a protective sheet that covers a portion of the main body,
   wherein the protective sheet is square, rectangular, or L-shaped and secured to the main body along at least three sides to form the pocket with a foot pedal and cable opening along a fourth side of the protective sheet to enable insertion of the at least one foot pedal into the pocket through the foot pedal and cable opening, thereby protecting the at least one foot pedal from blood or irrigation fluid falling from the operating room table during the surgical procedure
   wherein when the foot pedal is inside the pocket, a cable for connecting the foot pedal to the surgical equipment extends through the foot pedal and cable opening on the fourth side of the protective sheet, and
   wherein the protective sheet is a clear plastic sheet through which the foot pedal is visible.

2. An operating room floor mat as claimed in claim 1, wherein the protective sheet is square or rectangular.

3. An operating room floor mat as claimed in claim 1, wherein at least one of the main body and the protective sheet is L-shaped.

4. An operating room floor mat as claimed in claim 1, wherein the main body is made of or includes a layer of non-slip material configured to absorb the irrigation fluid and blood.

* * * * *